US009951819B2

(12) United States Patent
Capoldi

(10) Patent No.: US 9,951,819 B2
(45) Date of Patent: Apr. 24, 2018

(54) SLEWING ROLLER BEARING WITH SENSING PROBE

(71) Applicant: Aktiebolaget SKF, Gothenburg (SE)

(72) Inventor: Bruno Capoldi, Charentenay (FR)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 15/591,567

(22) Filed: May 10, 2017

(65) Prior Publication Data
US 2017/0350453 A1 Dec. 7, 2017

(30) Foreign Application Priority Data

Jun. 6, 2016 (DE) .................. 10 2016 209 889

(51) Int. Cl.
| | | |
|---|---|---|
| *F16C 41/00* | (2006.01) | |
| *F16C 19/36* | (2006.01) | |
| *G01N 29/04* | (2006.01) | |

(52) U.S. Cl.
CPC ............ *F16C 41/007* (2013.01); *F16C 19/36* (2013.01); *G01N 29/043* (2013.01); *G01N 2291/044* (2013.01); *G01N 2291/2696* (2013.01)

(58) Field of Classification Search
CPC .................................................. F16C 41/007
USPC ....................................................... 384/448
See application file for complete search history.

(56) References Cited

U.S. PATENT DOCUMENTS

| | | | | | |
|---|---|---|---|---|---|
| 4,798,299 | A | * | 1/1989 | Bayer | B66C 23/84 212/282 |
| 5,074,677 | A | * | 12/1991 | Andree | B66C 23/84 384/448 |
| 5,104,239 | A | * | 4/1992 | Sague | F16C 19/38 29/898.01 |
| 5,971,619 | A | * | 10/1999 | Bourgeois-Jacquet | F16C 19/166 384/448 |
| 6,113,276 | A | * | 9/2000 | Bourgeois-Jacquet | F16C 19/362 324/207.25 |
| 7,481,620 | B2 | * | 1/2009 | Kirsch | F16C 33/58 415/229 |
| 8,376,622 | B2 | * | 2/2013 | Claus | F16C 19/52 320/108 |
| 2014/0248014 | A1 | * | 9/2014 | Schmid | F16C 41/007 384/448 |
| 2016/0312835 | A1 | * | 10/2016 | Nicolas | G01D 5/244 |

* cited by examiner

*Primary Examiner* — Thomas R Hannon
(74) *Attorney, Agent, or Firm* — Bryan Peckjian; SKF USA Inc. Patent Dept.

(57) ABSTRACT

The invention relates to a slewing bearing that includes an inner ring, an outer ring, at least one row of rolling elements arranged between the rings in order to form an axial thrust that transmits axial forces, and at least one row of rolling elements arranged between the rings in order to form a radial thrust which can transmit radial forces. The slewing bearing further includes a sensing probe for detecting a relative displacement between the inner ring and outer ring and/or cracks, the inner ring having a through hole in which the sensing probe arranged. The through hole has a probe positioning element provided with a positioning portion and a support portion on which the sensing probe is supported so as to face the outer ring.

9 Claims, 3 Drawing Sheets

SLEWING ROLLER BEARING WITH SENSING PROBE

CROSS REFERENCE TO RELATED APPLICATIONS

This application claims priority to German patent application no. 102016209889.6 filed on Jun. 6, 2016, the contents of which are fully incorporated herein by reference.

FIELD OF THE INVENTION

The invention relates to the field of roller bearings, in particular roller bearings of large diameter for use in lifting machines such as a crane, or any other rotating applications of large dimensions.

BACKGROUND OF THE INVENTION

Roller bearings typically comprise an inner ring, an outer ring and at least two rows of rolling elements, such as rollers, arranged between the rings. Roller bearings of large diameter are generally loaded both radially and axially with relatively large loads. In this case, reference is made to an orientation roller bearing or slewing roller bearing.

Patent application FR-A1-2 694 610 describes a slewing roller bearing comprising three row of rollers arranged between the inner and outer rings, and wherein two rows make it possible to withstand axial forces. The third row of rollers makes it possible to withstand radial forces, and is arranged between the cylindrical outer surface of the inner ring, and a groove formed in the bore in the outer ring.

As a result of heavy loads, parts of the bearing, more particularly raceways of the rollers, wear out. This wear leads to displacements of the rings relative to each other and therefore relative movements of elements connected to the rings. Such unwanted movements affect to proper functioning of the bearing and the application, with the risk that the bearing rings come in contact and collide. Other elements attached to the bearing rings may also collide. Cracks of the bearing parts may also resulted from heavy loads.

It is common to replace the bearings when they are worn out. Such maintenance interventions are expensive, especially because of the downtime need for the machines or facilities.

It is therefore desirable that such maintenance interventions are timely performed before any contact between the bearing rings, but not too early too. It is desirable that such maintenance interventions are only performed when needed.

BRIEF SUMMARY OF THE INVENTION

The aim of the invention is to solve the above difficulties. It is proposed a slewing roller bearing with efficient means to anticipate the bearing wear, of reduced costs of installation, use and maintenance, with a longer service life and with an improved assembly process.

To this end, the invention relates to a slewing bearing comprising an inner ring, an outer ring and at least one row of rolling elements arranged between the rings in order to form an axial thrust which can transmit axial forces, and at least one row of rolling elements arranged between the rings in order to form a radial thrust which can transmit radial forces.

According to the invention, the slewing bearing further comprises a sensing probe, in particular for detecting a relative displacement between the inner and outer rings and/or cracks. The inner ring comprises a through hole with a cavity wherein is arranged the sensing probe, the cavity extending longitudinally between an outer opening facing the outer ring and an inner opening on the opposite side to the outer ring, the inner and outer openings being offset. The through hole further comprises a probe positioning element arranged in the cavity and provided with a positioning portion between the inner and outer openings of the through hole, and a support portion arranged at the outer opening and on which the sensing probe is supported so as to face the outer ring by the outer opening.

Thanks to the invention, a sensing probe is provided to the slewing bearing for monitoring the bearing condition during its service life. Risks of damage and cracks can be anticipated during bearing service life. Maintenance operations can be planned according to the sensing probe measurements and only when wear is going to happen.

The inner and outer openings are offset, and both can be arranged in an appropriate position on the inner ring. More particularly, the inner opening which is dedicated to receive the sensing probe when it is assembled in the through hole of the bearing can be positioned at a given position that is easy to access for an operator. The position may depend on the dimensions of slewing bearing, application arrangement and external parts fixed to the inner ring. The position of the outer opening is to be set precisely relative to the outer ring so as to accurately detect the relative displacement between the inner and outer rings.

Thanks to the probe positioning element provided in the through hole, the inner and outer openings do not need to be positioned relatively to each other. A sensing probe is inserted by the inner opening and is arranged in its final position at outer opening through the positioning portion of the probe positioning element.

Another advantage of the invention is that a standardized inner ring may receive a plurality of types and dimensions of sensing probes, the positioning being adapted by specific probe positioning element.

According to further aspects of the invention which are advantageous but not compulsory, such a slewing bearing may incorporate one or several of the following features:

The cavity comprises a first portion opened to the inner opening and a second portion opened to the outer opening, the second portion of cavity being of larger dimensions than the first portion.

The inner opening is sealed by a plug.

The outer opening is of larger dimensions than the inner opening.

The outer opening is partially closed by the probe positioning element arranged in the cavity.

The positioning portion of the probe positioning element comprises a sloped surface on which the sensing probe is dedicated to slide at assembly.

The cavity of the through hole is longitudinally open on a front surface of the inner ring, the through hole being dedicated to be closed on the front surface by a chassis.

The probe positioning element comprises a fixing portion dedicated to be fixed to inner ring or to a chassis.

The sensing probe is an ultrasound probe.

The sensing probe is in direct contact with the outer ring.

Pre-stressing means are arranged between the plug and the sensing probe to maintain contact between the sensing probe and the outer ring.

The sensing probe is connected to a control unit arranged outside from the slewing bearing.

The probe positioning element comprises sealing means comprising at least one sealing lip in sliding contact with the outer ring.

The inner ring comprises an inner bore provided with gear teeth, a through passage being provided through the gear teeth towards the inner opening of the through hole.

Rolling elements arranged between the inner and outer rings and forming an axial thrust are rollers.

Rolling elements arranged between the inner and outer rings and forming a radial thrust are rollers.

BRIEF DESCRIPTION OF THE SEVERAL VIEWS OF THE DRAWING

The invention will now be explained in correspondence with the annexed figures, as illustrative examples, without restricting the object of the invention. In the annexed figures.

DETAILED DESCRIPTION OF THE INVENTION

Figure 1:
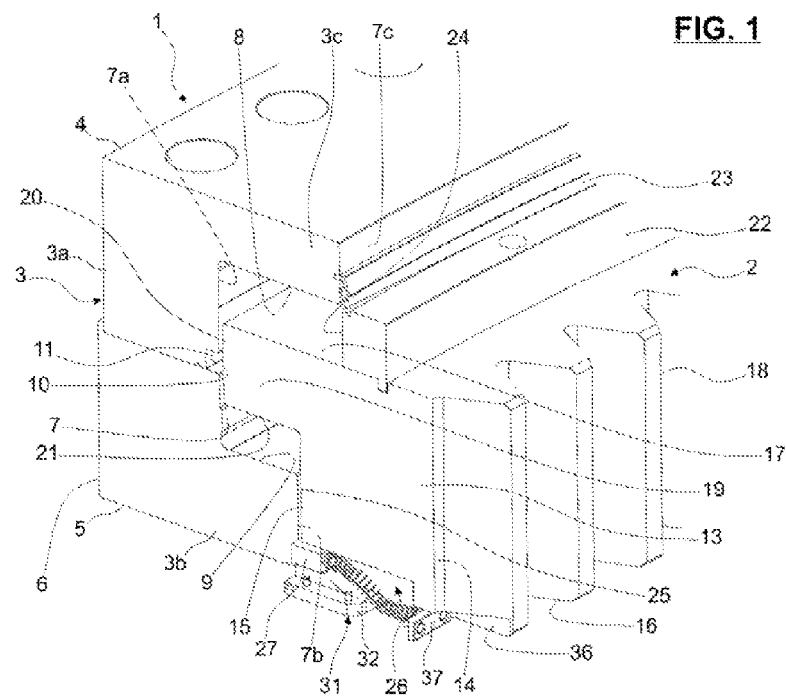
FIG. 1 is a perspective sectional view of a slewing bearing according to a first embodiment of the invention.
Figure 2:
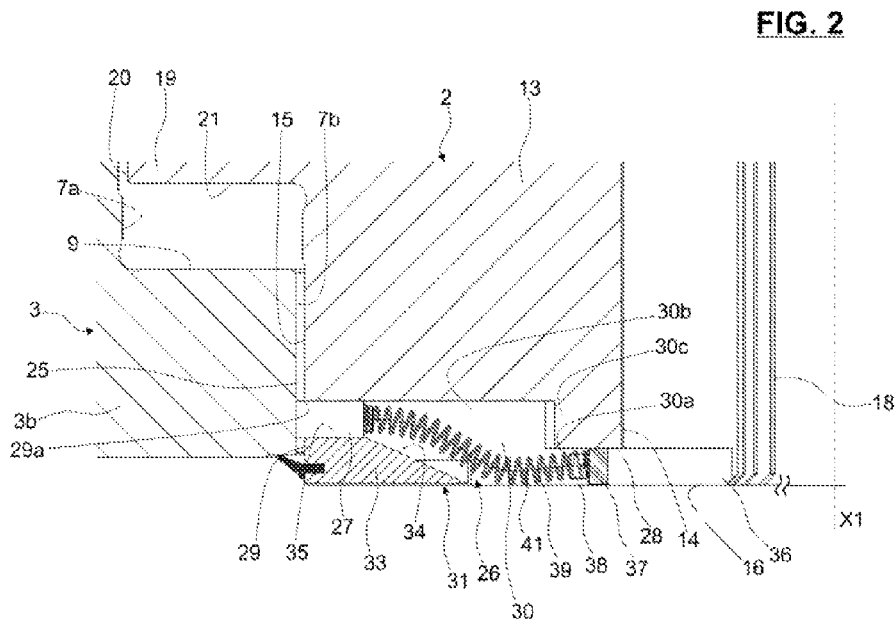
FIG. 2 is an enlarged sectional view of the slewing bearing.

FIGS. 1 and 2 show a slewing roller bearing 1 with a large diameter which can be used in particular in lifting machines such as a crane, or any other rotating applications of large dimensions.

The slewing roller bearing 1 with a central axis X1 comprises an inner ring 2, an outer ring 3, two rows of rollers (not shown) arranged between the the rings 2, 3 in order to form an axial thrust which can transmit axial forces, and one row of rollers (not shown) arranged between the the rings 2, 3 in order to form a radial thrust which can transmit radial forces.

Hereinafter, the adjectives "axial" and "radial" are defined relative to the central axis X1 of the slewing roller bearing 1.

The inner ring 2 and the outer ring 3 are concentric, and extend axially along the axis of rotation X1 of bearing 1.

As one embodiment, the outer ring 3 is made of two main parts 4, 5 which are assembled to one another by any appropriate means, for example by being bolted.

The outer ring 3 comprises a cylindrical outer surface 6 and a stepped bore 7 on which there are formed first, second and third raceways 8, 9 and 10 respectively. The outer ring 3 has a C-shape with a cylindrical portion 3a, a lower annular radial portion 3b and an upper annular radial portion 3c, the stepped bore 7 defining a first, second and third bore portions 7a, 7b and 7c, respectively.

The first raceway 8 is provided to the upper radial portion 3c. Raceway 8 is in the form of an annular radial surface which is in linear contact with rollers. The radial raceway 8 is extended, at the level of an edge with a large diameter, by the cylindrical axial bore portion 7a of the stepped bore 7 which delimits locally the third raceway 10.

The third raceway 10 is provided to the cylindrical portion 3a. Raceway 10 is arranged in a groove 11 formed in the bore portion 7a and extends radially towards the exterior of the bearing 1. The base of the groove 11 is offset radially towards the exterior relative to the bore portion 7a, and forms the third raceway 10. The axial raceway 10 is in the form of an annular axial surface which is in linear contact with rollers.

The bore portion 7a is extended radially, on the side opposite to the first raceway 8, by the lower radial portion 3b. Second raceway 9 is provided to the radial portion 3b and is in the form of an annular radial surface in linear contact with rollers.

The inner ring 2 comprises a cylindrical annular body 13 radially delimited by a cylindrical bore 14 and an outer cylindrical surface 15, and axially delimited by two opposite lateral radial surfaces 16, 17. The cylindrical bore 13 is provided with gear teeth 18 designed to cooperate with a corresponding structure or machine or frame (not represented).

The cylindrical annular body 13 comprises an outwardly projecting portion 19. The portion 19 protrudes radially from the outer cylindrical surface 15 towards the outer ring 3. Portion 19 is axially arranged between the radial portions 3b and 3c of the outer ring 3. The portion 19 is radially delimited by an outer cylindrical surface 20 that is radially opposite to the third raceway 10 of outer ring 3, and forming an axial raceway for a row of rollers radially arranged between the raceways 10 and 20. The portion 19 is axially delimited by an upper lateral radial surface that is in the extension of the upper lateral radial surface 17 of the cylindrical annular body 13. The upper lateral radial surface 17 is axially opposite to the first raceway 8 of outer ring 3, and forms a radial raceway for a row of rollers axially arranged between the raceways 8 and 17. The portion 19 is further axially delimited by a lower radial surface 21 that is axially opposite to the second raceway 9 of outer ring 3, and forms a radial raceway for a row of rollers axially arranged between the raceways 8 and 21.

The inner ring 2 is further provided with a sealing ring 22. The ring is provided to the upper lateral radial surface 17 and axially extends towards the upper radial portion 3c of outer ring 3. The sealing ring 22 comprises a seal lip 23 in sliding contact with the bore portion 7c of the portion 3c. The sealing ring 22 defines an outer cylindrical surface 24. The sealing ring 22 is fixed to the inner ring 2 by any appropriate means. As an alternate embodiment, the sealing ring is formed integrally with the inner ring 2.

The raceway 21 of outwardly projecting portion 19 and the lower lateral radial surface 16 of cylindrical annular body 13 are axially offset. The raceway 20 of outwardly projecting portion 19 and the outer cylindrical surface 15 of cylindrical annular body 13 are radially offset. The outer cylindrical surface 24 of the sealing ring 22 and the raceway 20 of outwardly projecting portion 19 are radially offset.

The bore portion 7a of the stepped bore 7 of outer ring 3 and the outer cylindrical surface 15 of inner ring 2 form radial abutments for the rollers arranged between the raceways 9 and 21. The bore portion 7a of the stepped bore 7 of outer ring 3 and the outer cylindrical surface 24 of the sealing ring 22 form radial abutments for the rollers arranged between the raceways 8 and 17.

The bore portion 7b of the lower radial portion 3b of outer ring 3 is radially facing the outer cylindrical surface 15 of the cylindrical annular body 13 of inner ring 2. The bore portion 7b and outer cylindrical surface 15 are radially spaced by a gap 25.

According to the invention, the inner ring 2 of slewing roller bearing 1 further comprises a radial through hole 26 wherein is arranged a sensing probe 27 for detecting a relative displacement between the inner ring 2 and the outer ring 3 and/or cracks of the rings 2, 3.

Figure 3:
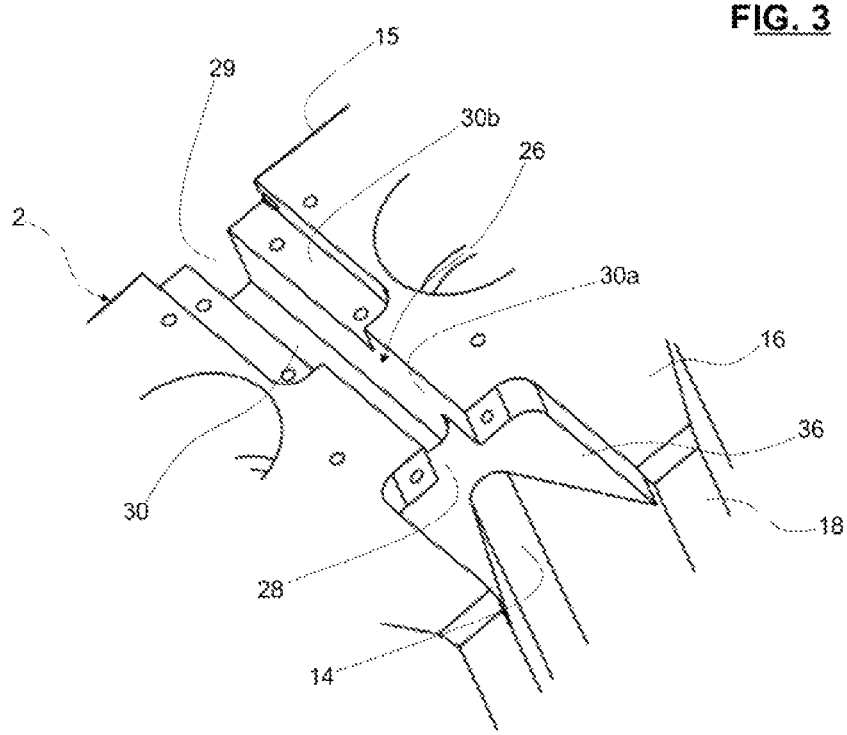
FIG. 3 is a perspective bottom view of an inner ring of the slewing bearing.

As illustrated in FIG. 3, the radial through hole 26 is provided through the radial thickness of inner ring 2. Through hole 26 comprises a first inner opening 28 opened towards the central axis X1 of bearing 1. Through hole 26 comprises a second outer opening 29 opened towards the outer ring 3. The outer opening 29 radially faces the bore portion 7b of the lower radial portion 3b of outer ring 3. The outer opening 29 has radial dimension greater than the inner opening 28. A cavity 30 is radially defined between the inner opening 28 and outer opening 29. Cavity 30 comprises a first portion 30a in the radial extension of the inner opening 28 and a second portion 30b in the radial extension of the outer opening 29. Since the openings 28, 29 have different radial dimensions, a shoulder 30c is defined in the cavity 30 at the junction between first portion 30a and second portion 30b of cavity.

The radial through hole 26 is provided to the lower lateral radial surface 16 of inner ring 2, the through hole 26 being opened to the surface 16. The through hole 26 is dedicated to be axially closed on the lower radial surface 16 by a non-illustrated chassis fixed to the inner ring 2.

Figure 4:
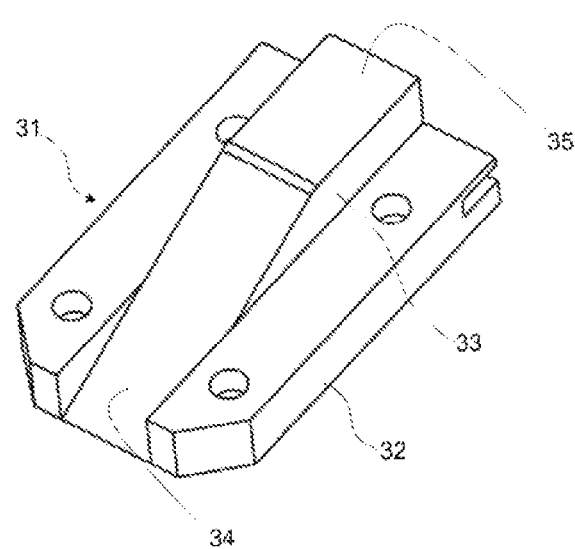
FIG. 4 is a perspective top view of a probe positioning element of the slewing bearing.

The radial through hole 26 comprises a probe positioning element 31 arranged within cavity 30. Probe positioning element 31 is radially offset from the inner opening 28 towards the outer ring 3. Probe positioning element 31 partly closes the outer opening 29 of through hole 26. As illustrated in the FIG. 4, the probe positioning element 31 comprises a base portion 32 provided with fixing means dedicated to be fixed to a chassis support surface supporting the inner ring 2. The fixing means may comprise screws, pins or any other appropriate means. The base portion 32 of element 31 is in the form of a radial plate. The probe positioning element 31 comprises a positioning portion 33 that axially extends from the base 31 and directed towards the inner ring 2. The positioning portion 33 comprises an outer sloped surface 34 that is radially extended by a support radial surface 35. Sloped surface 34 starts at the level of the bottom of inner opening 28 of through hole 26, more precisely sloped surface 34 starts from the chassis support surface. Sloped surface 34 forms an angle with the central axis X1 towards the inner ring 2. Sloped surface 34 is inclined from the level of the bottom of inner opening 28 to an upper position in the outer opening 29 of through hole 26. Sloped portion 34 is radially extended by a radial surface 25 up to the outer opening 29. The outer opening 29 is partly axially closed by the probe positioning element 31 so as to define a free outer opening 29a.

Sensing probe 27 is received by through hole 26 in inner ring 2. Sensing probe 27 is axially supported by the radial surface 35 of the probe positioning element 31. Sensing probe 27 is arranged at the free outer opening 29a so as to radially face the outer ring 3. In the illustrated embodiment, the sensing probe 27 is an ultrasound probe that comes radially into contact with the bore portion 7b of the inner ring 3 through the outer opening 29. Alternatively, the sensing probe 27 does not contact the outer ring 3, axial gap 25 separating the probe 27 and ring 3. The axial position of the sensing probe is precisely set, particularly the radial position of the radial surface 35, for an accurate detection by the probe positioning element 31.

Inner opening 28 and free outer opening 29a are axially offset. The free outer opening 29a has to be precisely defined to accurate sensing probe detection. Inner opening 28 is defined at the lower radial surface 16 of the inner ring 2 for an optimized position. A radial passage 36 through the gears 18 has to be defined to access to the inner opening 28. In this position, the radial passage 36 is easy to manufacture and of minimal radial dimensions to permit the sensing probe insertion.

Sensing probe 27 can be easily inserted into the radial through hole 28 and placed in its final position. More precisely, an operator radial inserts the sensing probe 27 through the radial passage 36 provided through the gears 18 towards the inner opening 28 of radial through hole 26. Sensing probe 27 is radially inserted in the cavity 30 up to the sloped surface 34 of the probe positioning element 31. Sensing probe is slid on the sloped surface 34 from the bottom level of the inner opening 28 towards the level of the free outer opening 29a of outer opening 29. Sensing probe 27 is slid from the sloped surface 34 to the radial surface 35 until radial abutment with the bore portion 7b of the lower radial portion 3b of outer ring 3. Sensing probe 27 is then in its final position.

Figure 5:
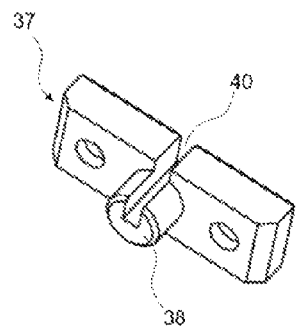
FIG. 5 is a perspective top view of a plug of the slewing bearing.

In the illustrated embodiment, the inner opening 28 is sealed by a plug 37. The plug 37 is fixed between the inner ring 2 and the support surface of the chassis by any appropriate means, for example by force-fitting. As illustrated in the FIG. 5, the plug 37 comprises a pin 38 that radially outwardly extends towards the sensing probe 27. The pin 28 forms a radial support for a spring 39 radially arranged between the plug 37 and sensing probe 27. Spring 39 exerts a radial pre-stressing load on the sensing probe 27 so as to ensure a constant contact between the probe 27 and the outer ring 3 in case of relative displacement between the rings 2, 3. The plug 37 further comprises a through opening 40 wherein a cable 41 can go through. The cable 41 connect sensing probe 27 to a non-illustrated control unit so as to transmit sensed measurements.

Figure 6:
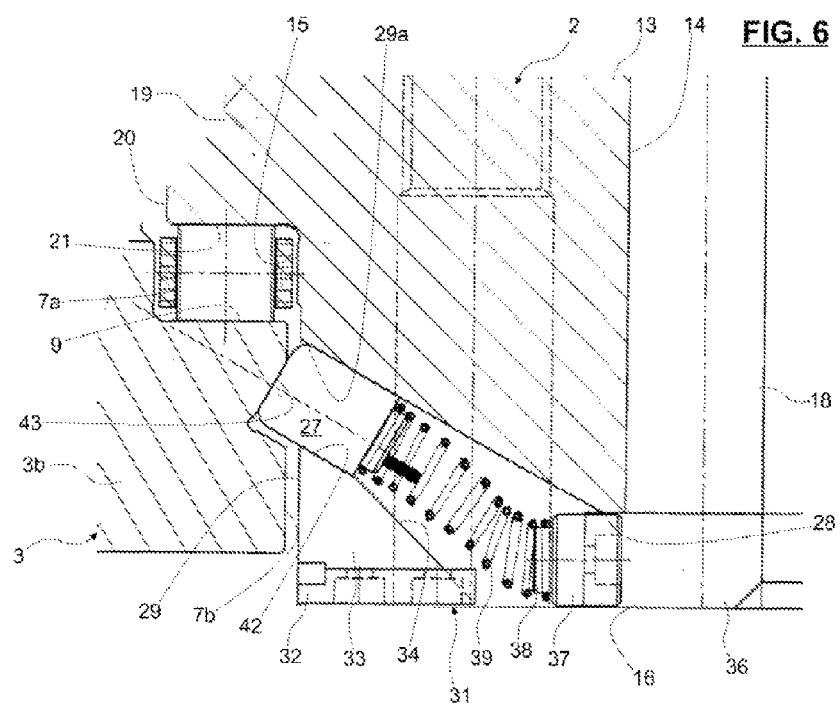
FIG. 6 is an enlarged sectional view of a slewing bearing according to a second embodiment of the invention

A second embodiment of the invention is illustrated in FIG. 6, wherein the same elements have the same references, differs from the first embodiment of FIGS. 1 and 2 in that a support surface 42 for the sensing probe 27 is inclined with respect to the central axis X1.

The sloped surface 34 of the probe positioning element 31 starts from the bottom level of the inner opening 28 at the support surface of the chassis and is further extended by a sloped support surface 42 to the free outer opening 29 of outer opening 29. Sensing probe 27 is then inclined with respect to the outer ring 3.

The outer ring 3 comprises a contact surface 43 provided in the bore portion 7c, the contact surface 43 being inclined with respect to the central axis X1 and in a perpendicular plan to the sensing probe 27.

Advantageously, an ultrasound sensing probe 27 can more accurately measure the relative displacement of the outer ring 3 with the inner ring 2, and more precisely the displacement of the edge of raceway 9.

The invention claimed is:

1. A slewing bearing comprising:
an inner ring,
an outer ring,
at least one row of rolling elements arranged between the rings in order to form an axial thrust which can transmit axial forces, and
at least one row of rolling elements arranged between the rings in order to form a radial thrust which can transmit radial forces, and
a sensing probe for detecting a relative displacement between the inner ring and outer ring and/or cracks, the inner ring having a through hole with a cavity in which the sensing probe is disposed, the cavity extending longitudinally between an outer opening facing the outer ring and an inner opening on the opposite side to the outer ring, the inner opening and outer opening being offset, the through hole further providing a probe positioning element arranged in the cavity and provided with a positioning portion between the inner opening and outer opening, and a support portion arranged at the outer opening and on which the sensing probe is supported so as to face the outer ring by the outer opening.

2. The slewing bearing according to claim 1, wherein the inner opening is sealed by a plug.

3. The slewing bearing according to claim 2, wherein pre-stressing means are arranged between the plug and the sensing probe to maintain contact between the sensing probe and the outer ring.

4. The slewing bearing according to claim 1, wherein the outer opening is larger than the inner opening, the outer opening being partially closed by the probe positioning element arranged in the cavity.

5. The slewing bearing according to claim 1, wherein the positioning portion of the probe positioning element provides a sloped surface on which the sensing probe is dedicated to slide.

6. The slewing bearing according to claim 1, wherein the cavity of the through hole is longitudinally open on a front surface of the inner ring, the through hole being dedicated to be closed on the front surface by a chassis.

7. The slewing bearing according to claim 1, wherein the probe positioning element provides a fixing portion dedicated to be fixed to inner ring or to a chassis.

8. The slewing bearing according to claim 1, wherein the sensing probe is an ultrasound probe.

9. The slewing bearing according to claim 1, wherein the sensing probe is in direct contact with the outer ring.

* * * * *